(12) United States Patent
Militz et al.

(10) Patent No.: US 9,839,461 B2
(45) Date of Patent: Dec. 12, 2017

(54) EXPANSION DEVICE FOR BONE EXPANSION AND MEDICAL DEVICE FOR BONE EXPANSION

(76) Inventors: Matthias Militz, Murnau (DE); Markus Oehlbauer, Murnau (DE)

(*) Notice: Subject to any disclaimer, the term of this patent is extended or adjusted under 35 U.S.C. 154(b) by 596 days.

(21) Appl. No.: 14/239,399

(22) PCT Filed: Jul. 27, 2012

(86) PCT No.: PCT/EP2012/064838
§ 371 (c)(1),
(2), (4) Date: Apr. 9, 2014

(87) PCT Pub. No.: WO2013/023898
PCT Pub. Date: Feb. 21, 2013

(65) Prior Publication Data
US 2014/0222094 A1 Aug. 7, 2014

(30) Foreign Application Priority Data

Aug. 18, 2011 (DE) .......... 10 2011 110 995
May 11, 2012 (DE) .......... 10 2012 207 968

(51) Int. Cl.
| | |
|---|---|
| *A61B 17/88* | (2006.01) |
| *A61B 17/72* | (2006.01) |
| *A61B 17/68* | (2006.01) |

(52) U.S. Cl.
CPC ...... *A61B 17/8858* (2013.01); *A61B 17/7275* (2013.01); *A61B 17/8855* (2013.01); *A61B 2017/681* (2013.01); *F04C 2270/0421* (2013.01)

(58) Field of Classification Search
CPC ....... A61B 17/68; A61B 17/88; A61B 17/885; A61B 17/8852; A61B 17/8855; A61B 17/8858; A61B 2017/681
See application file for complete search history.

(56) References Cited

U.S. PATENT DOCUMENTS

| | | | | |
|---|---|---|---|---|
| 5,919,163 A | * | 7/1999 | Glickman | .......... A61M 25/1011 604/101.05 |
| 6,264,659 B1 | * | 7/2001 | Ross | .................. A61B 17/8822 606/93 |
| 6,632,235 B2 | * | 10/2003 | Weikel | ................. A61B 17/025 606/192 |

(Continued)

FOREIGN PATENT DOCUMENTS

| | | |
|---|---|---|
| FR | 2 653 006 A1 | 4/1991 |
| JP | 2009-515600 | 4/2009 |
| WO | WO-2011/092268 A1 * | 4/2011 |

OTHER PUBLICATIONS

International Search Report for PCT/EP2012/064838 dated Nov. 23, 2012.

(Continued)

*Primary Examiner* — Christian Sevilla
*Assistant Examiner* — Eric S Gibson
(74) *Attorney, Agent, or Firm* — Sughrue Mion, PLLC

(57) ABSTRACT

The invention relates to an expansion device for bone expansion, wherein the expansion device has a proximal end and a distal end, between which ends the expansion device extends in a longitudinal direction, and extending apparatuses, which succeed one another in the longitudinal direction, wherein the extension apparatuses can be extended in order to exert force on a bone.

6 Claims, 10 Drawing Sheets

(56) References Cited

U.S. PATENT DOCUMENTS

| | | | | |
|---|---|---|---|---|
| 6,659,957 B1* | 12/2003 | Vardi | A61B 5/0095 | 600/467 |
| 8,728,081 B2* | 5/2014 | Lauchner | A61B 17/8855 | 604/101.05 |
| 9,179,959 B2* | 11/2015 | Rabiner | A61B 17/7097 | |
| 2001/0012950 A1* | 8/2001 | Nishtala | A61M 25/0662 | 606/198 |
| 2002/0031601 A1* | 3/2002 | Darouiche | A61L 29/005 | 427/2.1 |
| 2003/0032963 A1* | 2/2003 | Reiss | A61B 10/025 | 606/90 |
| 2003/0050702 A1* | 3/2003 | Berger | A61B 17/8855 | 623/17.12 |
| 2003/0181800 A1* | 9/2003 | Bonutti | A61B 17/0401 | 600/407 |
| 2004/0068226 A1* | 4/2004 | Brannon | A61M 25/1011 | 604/101.01 |
| 2004/0215140 A1* | 10/2004 | Forman | A61M 25/1011 | 604/101.01 |
| 2005/0209629 A1* | 9/2005 | Kerr | A61B 17/025 | 606/192 |
| 2006/0079905 A1* | 4/2006 | Beyar | A61B 17/7095 | 606/76 |
| 2006/0184192 A1* | 8/2006 | Markworth | A61B 17/1659 | 606/198 |
| 2006/0271061 A1* | 11/2006 | Beyar | A61B 1/00071 | 606/105 |
| 2007/0060924 A1* | 3/2007 | Choi | A61B 17/8855 | 606/93 |
| 2007/0250038 A1* | 10/2007 | Boulais | A61M 25/0026 | 604/523 |
| 2008/0097374 A1* | 4/2008 | Korleski | A61B 17/8855 | 604/500 |
| 2009/0005782 A1* | 1/2009 | Chirico | A61B 17/1617 | 606/63 |
| 2009/0005821 A1* | 1/2009 | Chirico | A61B 17/8685 | 606/319 |
| 2009/0012564 A1* | 1/2009 | Chirico | A61B 17/1671 | 606/246 |
| 2009/0182336 A1* | 7/2009 | Brenzel | A61B 17/7225 | 606/62 |
| 2009/0247664 A1* | 10/2009 | Truckai | A61L 24/0089 | 523/116 |
| 2009/0299327 A1* | 12/2009 | Tilson | A61B 17/8816 | 604/500 |
| 2010/0006102 A1* | 1/2010 | Schnell | A61M 16/04 | 128/207.14 |
| 2010/0198225 A1* | 8/2010 | Thompson | A61B 17/8858 | 606/90 |
| 2010/0241178 A1* | 9/2010 | Tilson | A61B 17/8816 | 606/86 R |
| 2010/0249793 A1* | 9/2010 | Truckai | A61B 90/98 | 606/92 |
| 2010/0274080 A1* | 10/2010 | Donovan | A61B 17/3421 | 600/104 |
| 2011/0077651 A1* | 3/2011 | Lozier | A61B 17/7258 | 606/62 |
| 2011/0092859 A1* | 4/2011 | Neubardt | A61F 2/441 | 600/594 |
| 2011/0202064 A1* | 8/2011 | O'Halloran | A61B 17/1671 | 606/94 |
| 2011/0213301 A1* | 9/2011 | Auyoung | A61B 17/7065 | 604/96.01 |
| 2011/0270295 A1* | 11/2011 | Litvack | A61B 17/0218 | 606/192 |
| 2011/0307072 A1* | 12/2011 | Anderson | A61B 17/8858 | 623/23.53 |
| 2011/0313356 A1* | 12/2011 | Rabiner | A61B 17/7275 | 604/103.02 |
| 2012/0029102 A1* | 2/2012 | Rose | A61B 17/72 | 521/88 |
| 2012/0083883 A1* | 4/2012 | Ginn | A61B 17/1604 | 623/17.11 |
| 2012/0165941 A1* | 6/2012 | Rabiner | A61B 17/7097 | 623/17.12 |
| 2012/0259355 A1* | 10/2012 | Druma | A61B 17/8855 | 606/192 |
| 2012/0265186 A1* | 10/2012 | Burger | A61B 17/8811 | 606/21 |
| 2012/0277811 A1* | 11/2012 | Lauchner | A61B 17/8855 | 606/86 R |
| 2012/0316491 A1* | 12/2012 | Jonsson | A61B 17/0057 | 604/26 |
| 2013/0013007 A1* | 1/2013 | Broome | A61B 17/8811 | 606/86 R |
| 2013/0144298 A1* | 6/2013 | Choi | A61M 25/0102 | 606/93 |
| 2013/0238038 A1* | 9/2013 | Auyoung | A61B 17/8855 | 606/86 R |
| 2014/0214085 A1* | 7/2014 | Druma | A61B 17/8855 | 606/279 |
| 2014/0222094 A1* | 8/2014 | Militz | A61B 17/7275 | 606/86 R |
| 2014/0277465 A1* | 9/2014 | Teisen | A61F 2/441 | 623/17.12 |
| 2014/0277466 A1* | 9/2014 | Teisen | A61F 2/441 | 623/17.12 |
| 2015/0112351 A1* | 4/2015 | Hsu | A61B 17/7097 | 606/92 |

OTHER PUBLICATIONS

Southerland, Joe T., D.P.M. et al., "Principles of Callus Distraction," Chapter 51, pp. 247-250.

\* cited by examiner

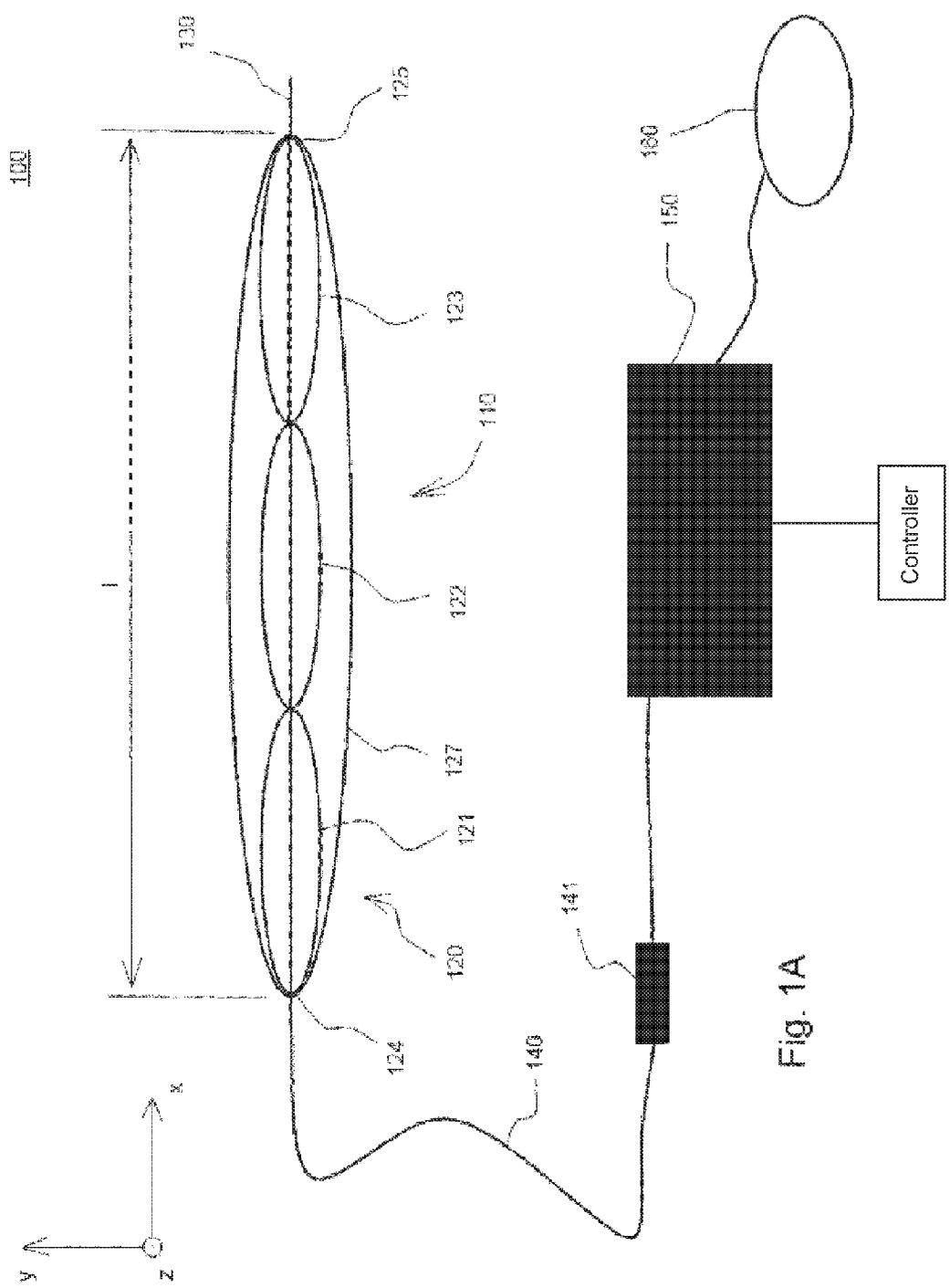

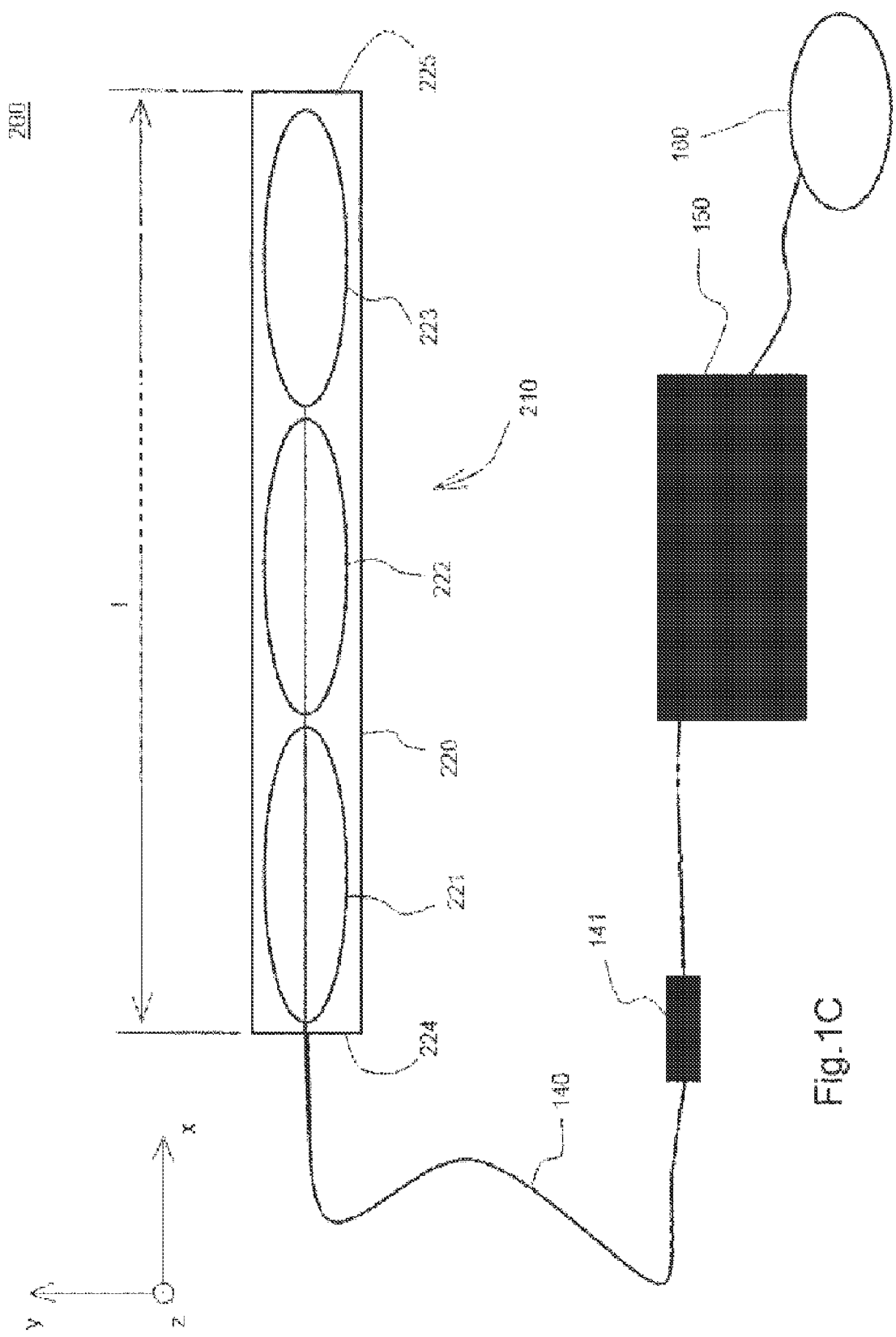

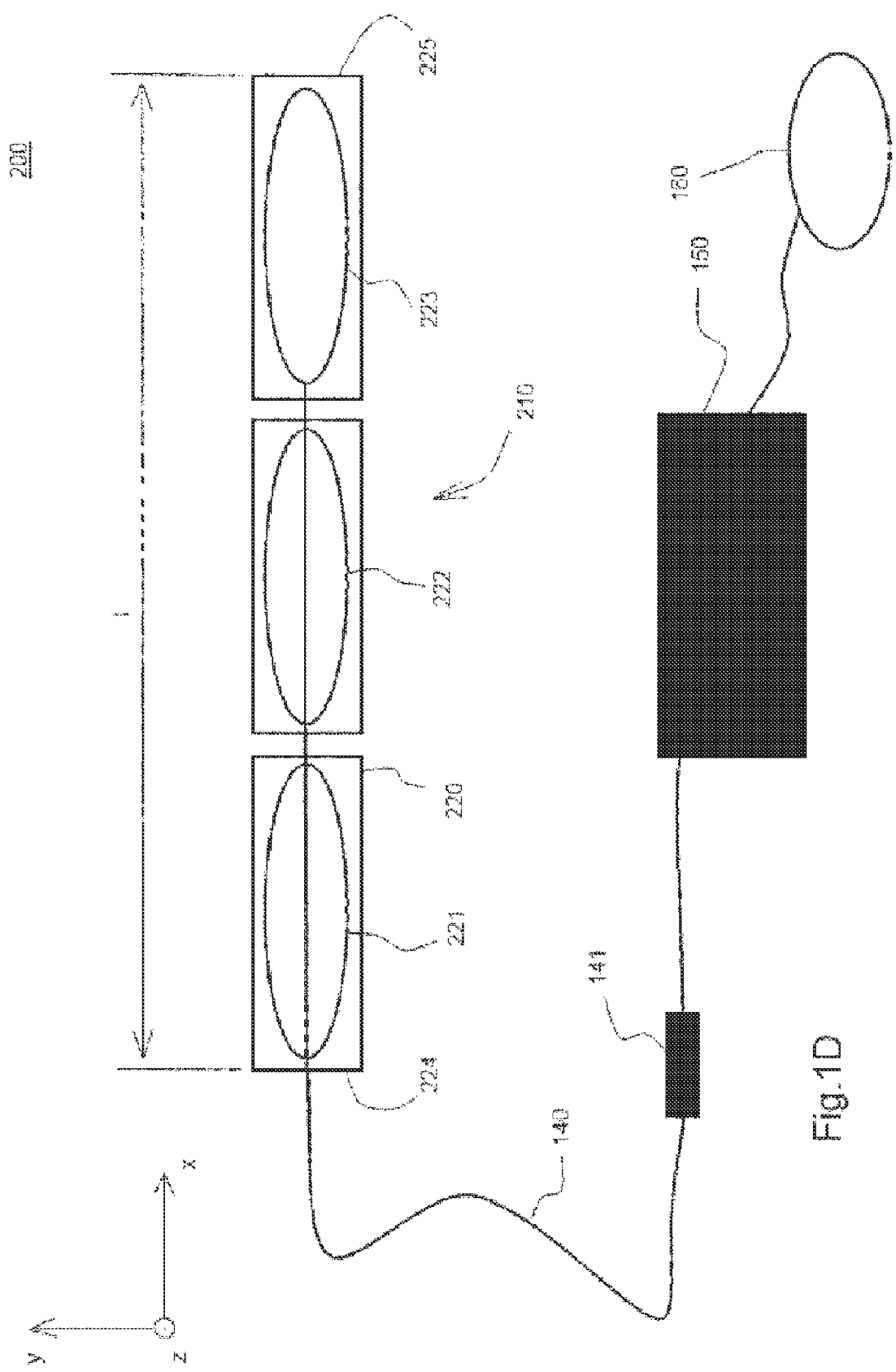

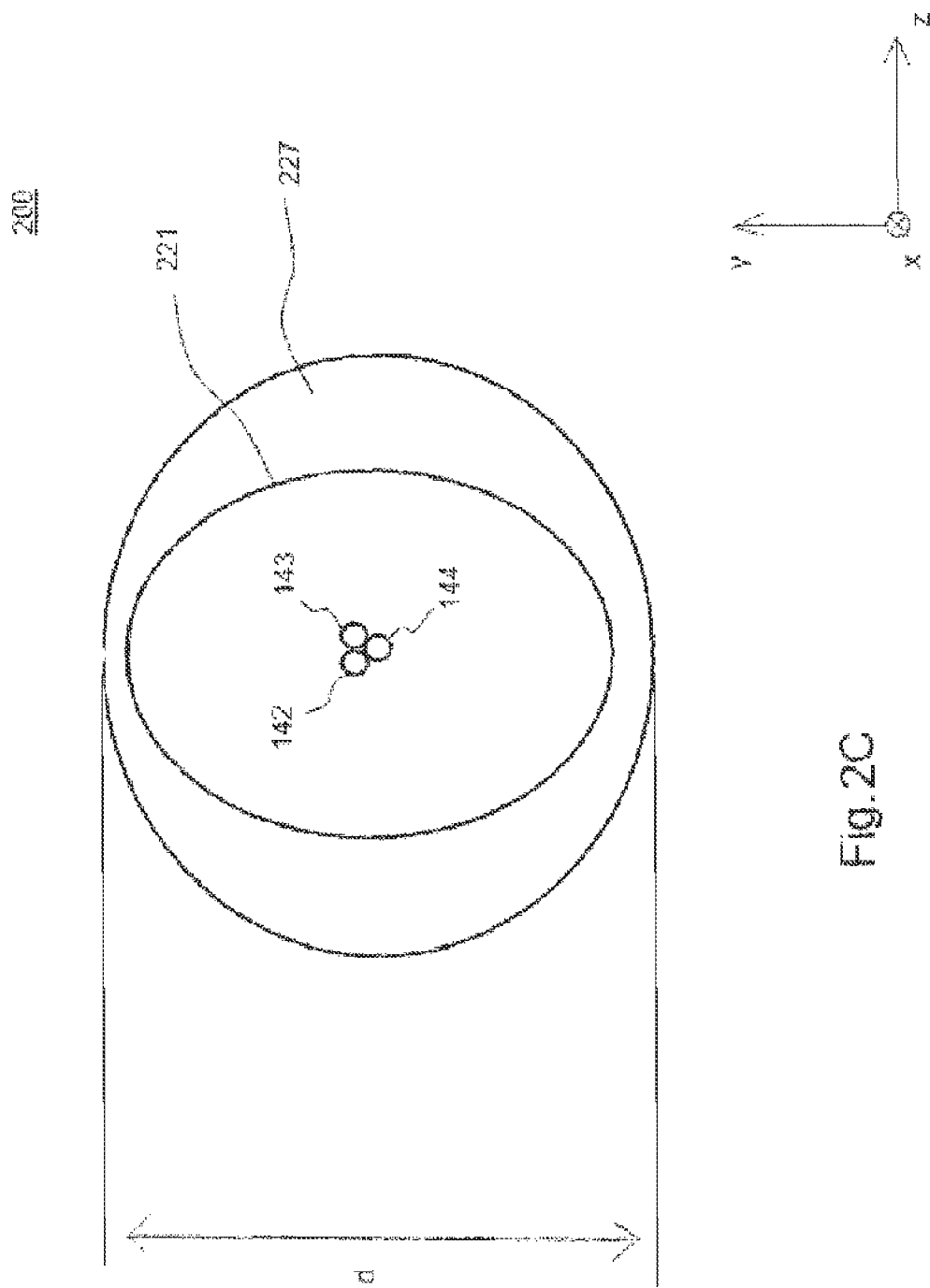

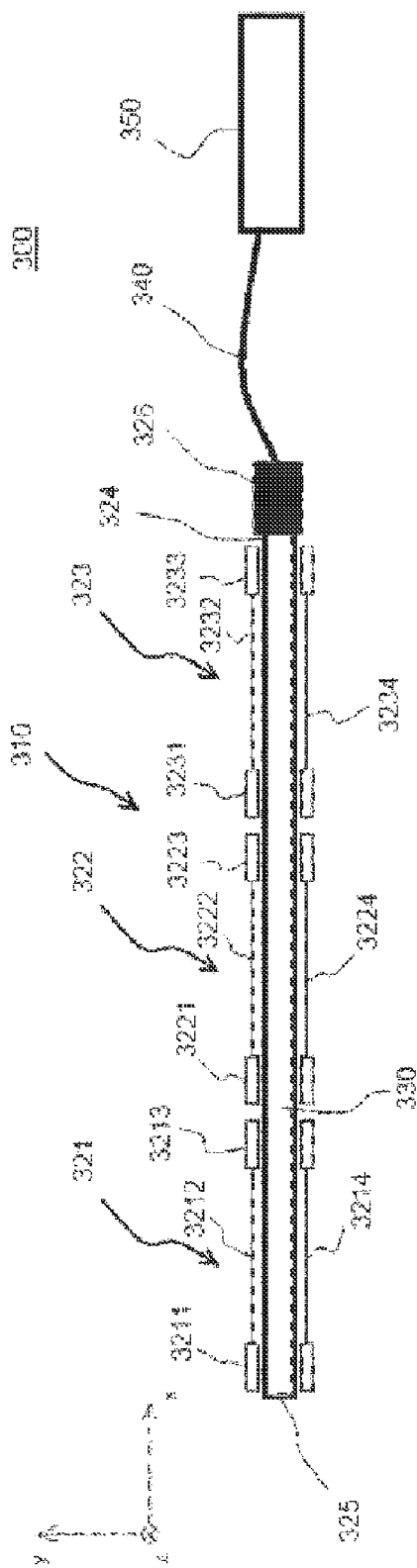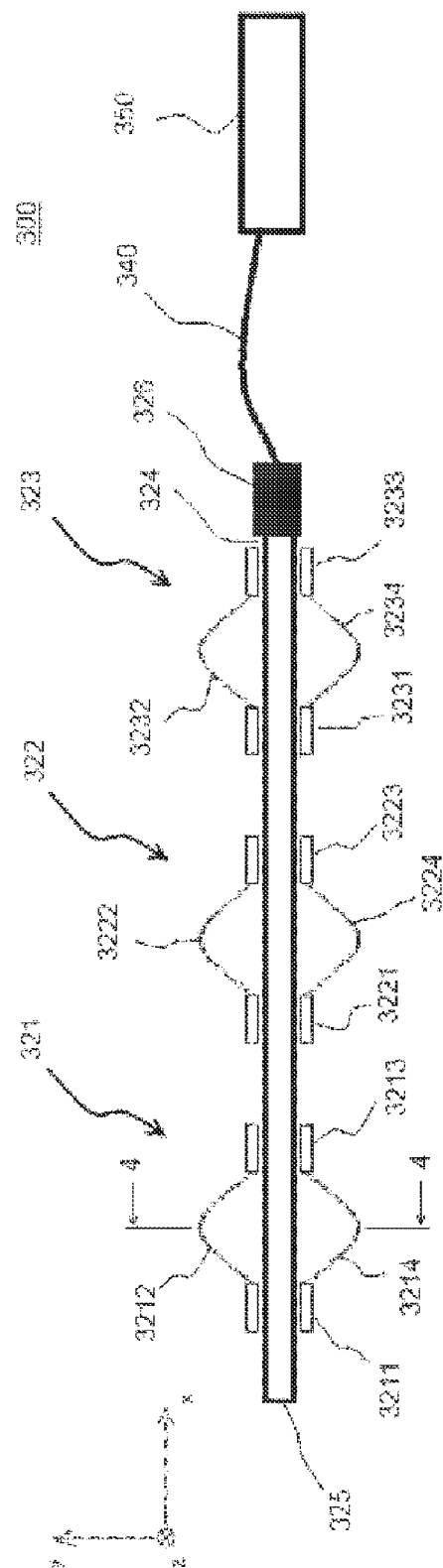

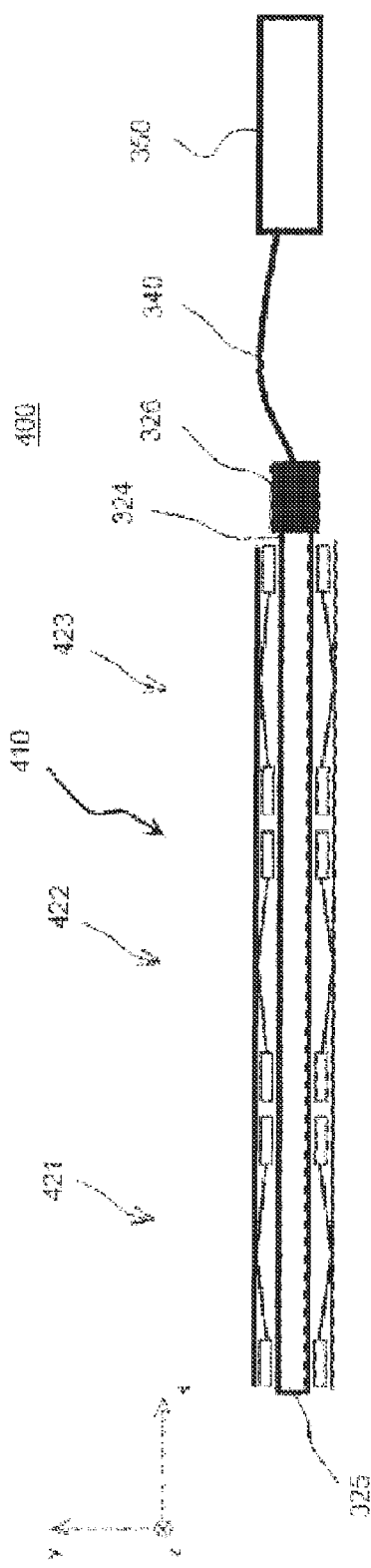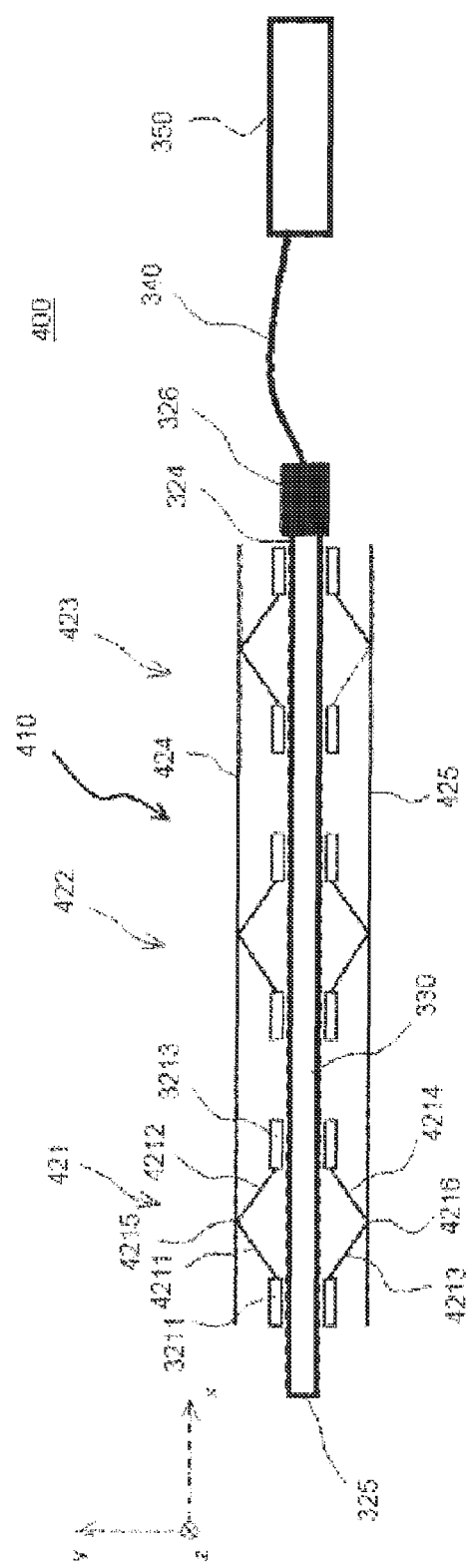

EXPANSION DEVICE FOR BONE EXPANSION AND MEDICAL DEVICE FOR BONE EXPANSION

CROSS REFERENCE TO RELATED APPLICATIONS

This application is a National Stage of International Application No. PCT/EP2012/064838 filed Jul. 27, 2012, claiming priority based on German Patent Application Nos. 10 2011 110 995.5 filed Aug. 18, 2011 and 10 2012 207 968.8 filed May 11, 2012, the contents of all of which are incorporated herein by reference in their entirety.

The present invention relates to an expansion device for bone expansion and a medical apparatus which comprises such an expansion device.

In the prior art, methods and corresponding devices for the treatment of defects in tubular bones are generally known in the medical field.

For example, the treatment of infections of tubular bones can lead to defects in the tubular bone which frequently measure several centimeters. The standard method for reconstruction of the absent tubular bone or for correction of the defect is callus distraction.

In this method, the two ends of the tubular bone at the defect are held by means of a fixing means such that the ends of the tubular bone at the defect are in contact with each other. After a certain time new bone tissue, the so-called callus, forms between the ends of the tubular bone at the defect.

The callus formed is then distracted via the fixing means by up to a maximum of 1 mm a day until the callus replaces the defect to be bridged in the tubular bone or the absent tubular bone. After consolidation of the distracted callus, i.e. the ossification of the newly formed bone tissue, the bone can be subjected to load again.

As can be seen from this, the method of callus distraction is protracted, depending on the size of the defect to be eliminated, and represents considerable stress to the patient.

Furthermore, the known method of callus distraction is associated with considerable technical measures, which result from the need to wear the fixing means over a long period of time. On the one hand the fixing means must be fixed to the defective tubular bone, and on the other hand it must be accessible externally for application of the tensile force. Implant-related complications frequently arise here, such as, for example, soft tissue irritation, which results from the fact that the tissue covering the tubular bone is necessarily tensioned by the fixing means during the callus distraction.

The object of the present invention is to provide a device which renders possible a rapid and simple reconstruction/treatment of a tubular bone.

This object is achieved with an expansion.

The basic concept of the invention is to correct a defect in a tubular bone by a procedure in which a tubular bone which the patient does not necessarily need for anatomical reasons, for example the calf bone (fibula), is slit in the longitudinal direction (osteotomy) and, after formation of the callus at the slit, is then expanded.

According to the invention, an expansion device for bone expansion is proposed, the expansion device having a proximal end and a distal end between which the expansion device extends in a longitudinal direction. According to the invention, the expansion device furthermore comprises expansion means which are arranged in succession in the longitudinal direction and can be expanded in order to exert a force on a bone.

The expansion device has dimensions between the proximal end and the distal end such that it can be inserted into a tubular bone to be expanded.

The expansion device according to the invention is inserted, when used as intended, into a tubular bone which is slit in the longitudinal direction (longitudinal osteotomy), and, after formation of the callus at the longitudinal slit, the expansion device is expanded along its longitudinal direction by expansion of the expansion means such that a tubular bone of larger cross-section is obtained as a result.

Due to the expansion device having a plurality of expansion means, the same or different forces can be exerted on sections of the tubular bone at which the corresponding expansion means are located, as a result of which the tubular bone can be expanded in a particular manner independently of its wall thicknesses in the longitudinal direction and its stability properties.

In other words, a tubular bone having desired dimensions can be obtained by the expansion device according to the invention. For example, the expansion means and can be expanded such that they expand evenly and uniformly i.e. such that the diameter of the tubular bone to be expanded increases in size uniformly over the entire length of the tubular bone. Depending on the wall thicknesses and stability properties of the tubular bone, it may be necessary here for different forces to be applied to the sections of the tubular bone via the expansion means.

However, the expansion means can also be expanded differently, i.e. not evenly and not uniformly. This is necessary, for example, if a tubular bone of non-constant diameter is to be obtained from a tubular bone of constant diameter.

Preferably, the expansion device and the expansion means, respectively, can be expanded radially.

The expansion device according to the invention is preferably also configured such that the expansion means can be expanded independently of each other.

In a preferred embodiment of the expansion device according to the invention, the expansion device comprises, for example, 2, 3, 4, 5, 6, 7, 8, 9, 10, 11, 12, 13, 14, 15, 16, 17, 18, 19, 20, 21, 22, 23, 24, 25, 26, 27, 28, 29 or 30 expansion means.

The expansion means of the expansion device according to the invention can be identical in construction, for example have the same size, and can be arranged either uniformly or non-uniformly in the longitudinal direction of the expansion device.

The expansion device according to the invention can also be constructed such that the expansion means are of different construction, for example have different sizes, and are arranged either uniformly or non-uniformly in the longitudinal direction of the expansion device, i.e. the distances between the expansion means can be either the same or different in the longitudinal direction.

Depending on how the expansion means are constructed and are arranged either uniformly or non-uniformly in the longitudinal direction, the expansion device according to the invention can be adapted, for example, to various tubular bones.

In a preferred embodiment of the expansion device according to the invention, the expansion means are accommodated in an encasing element which extends in the longitudinal direction between the proximal and distal end of the expansion device.

Preferred materials for the encasing element are, for example, a polyolefin-based elastomer, a silicone which is suitable for medical uses or generally a resilient polymer which is suitable for medical uses.

The encasing element advantageously accommodates the expansion means and preferably encloses them in a sealing manner, and for this reason it is possible for only the encasing element to be formed from a material which is suitable for implantation. That is to say the expansion means do not come into direct contact with the bone or bone marrow during the bone expansion or callus distraction, and for this reason the expansion means can be configured with regard to its materials merely with respect to the pressures and forces to be expected.

The expansion means can be, for example, chambers which can be filled independently of each other with a medium, such as, for example, a liquid, a gel or a gas.

The chambers are, for example, ellipsoidal or cylindrical in construction.

Depending on the number of chambers, it is possible to exert forces on sections of the tubular bone for radial expansion of the tubular bone.

For example, the chambers are formed by balloons, which can be filled with the medium independently of each other. Preferably, the balloons are formed from a resilient material, such as, for example, an elastomer, silicone, latex or generally from a resilient polymer.

In a further embodiment, the chambers can be constructed by segmenting a tube which extends in the longitudinal direction. For example, the chambers are formed in the tube by closing the flow channel of the tube at regular/irregular intervals.

Nevertheless, it is also possible to form each chamber by a tube closed on both sides and to arrange the tubes in succession in the longitudinal direction.

In order that the tube or tubes has/have certain extension properties when the medium is introduced, the tube or tubes has/have dimensions such that the internal diameter of the tube is not constant and different wall thicknesses of the tube or tubes thereby result.

A resilient material, such as, for example, an elastomer, silicone, latex or generally a resilient polymer, can likewise preferably be used as the material for the tubes.

Preferably, the chambers of the expansion device according to the invention can in each case be filled with the medium, i.e. the liquid, the gel or the gas, via a pressure tube.

Preferably, the pressure tube can be coated, at least in part, with a material or a substance which prevents bacterial colonization of the pressure tube. Such a coating can be, for example, an antibiotic layer, a silver layer or a silver-containing layer.

In a further embodiment, the expansion means can also be mechanical elements.

For example, the mechanical elements are spring elements which engage with a threaded spindle such that the spring elements are expanded by rotation of the threaded spindle.

Preferably, the mechanical spring elements have at least two, three or four leaf springs which engage indirectly or directly with the threaded spindle and are expanded by rotation of the threaded spindle.

In a preferred embodiment, the mechanical spring elements each have at least two, three or four leaf springs which are fixed on at least one sleeve which engages with the threaded spindle, and by rotation of the threaded spindle the sleeve can be displaced such that the leaf springs expand.

In a further preferred embodiment, the mechanical elements are scissor elements which engage with the threaded spindle such that the scissor elements are expanded by rotation of the threaded spindle.

Preferably, the expansion device has at least one force distribution element via which the expansion means, when the expansion device is used as intended, exert the force indirectly on the bone.

Such a force distribution element is, for example, a force distribution strut which is supported by a plurality of the mechanical elements and, when the expansion device is used as intended, i.e. during bone expansion, is arranged between the mechanical elements and the bone. By this means, the distribution of the force exerted on the bone is better.

In a further embodiment, the expansion means can be constructed such that they expand by absorption of body fluids.

The absorption of body fluids can be effected, for example, by the expansion means having a semipermeable membrane through which the fluid can be absorbed by the expansion means. Depending on how the membrane of such expansion means is constructed, the expansion means can expand uniformly or to different degrees and can also exert different forces on the tubular bone.

The absorption of the body fluids can take place, for example, by diffusion or osmosis.

In a further embodiment, the expansion means expanding by absorption of body fluids can be surrounded by an encasing layer which dissolves after a certain time (period of time for the callus formation), the expansion means then starting to expand.

In the case of expansion means which, after insertion of the expansion device into the tubular bone, cannot readily be changed in their expansion properties or their action of force on the tubular bone, it is advantageous to take CT X-rays of the tubular bone to be expanded before insertion of the expansion device and to adapt the expansion device or the expansion means individually to the corresponding bone according to the wall thicknesses or stability properties of the tubular bone.

To increase the stability of the expansion device, a metal core can run through the expansion device in the longitudinal direction. By this means the expansion device according to the invention can be arranged more easily within the tubular bone, for example through an intramedullary access. The metal core moreover can have dimensions such that it generates a good X-ray contrast, as a result of which the position of the expansion device according to the invention after insertion into the tubular bone can be readily checked.

The expansion device according to the invention preferably comprises on its outer surface at least one protrusion which is provided for prevention of a change in position of the expansion device within the tubular bone, i.e. in the inserted state. When the expansion device is inserted into the tubular bone through the intramedullary access, the at least one protrusion on the outer surface ensures that the expansion device does not rotate and does not change its position within the tubular bone.

Preferably, the at least one protrusion is constructed as a burl-like protrusion or as a bar extending in the longitudinal direction of the expansion device.

If the expansion means are constructed as chambers, the pressure tubes preferably run in the protrusion to the chambers.

Depending on the intended use of the expansion device according to the invention or depending on the length of the tubular bone into which the expansion device is to be inserted, the expansion device can be constructed differently in length, i.e. its length between the proximal and distal end can differ. Preferred lengths are 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 31 cm, 32 cm, 33 cm, 34 cm, 35 cm, 36 cm, 37 cm, 38 cm, 39 cm or 40 cm and can also lie between these values.

The expansion device according to the invention preferably has a diameter of between 1.5 cm and 3 cm in its maximum expanded state. In its base state, i.e. in its contracted or shrunk state, the diameter is preferably 0.2 cm to 0.4 cm.

According to the invention, a medical apparatus for bone expansion which comprises an expansion device explained above and an actuator which is set up to expand the expansion means of the expansion device is also provided.

If the expansion device comprises the embodiment of the expansion means as fillable chambers, the actuator is, for example, a pump which is set up such that it can fill the chambers with a medium.

If the expansion device is constructed in the embodiment of the expansion means as mechanical elements, the actuator is preferably an electric motor which is set up such that it can expand the mechanical elements. For example, the electric motor is connected or coupled with the threaded spindle explained above and can rotate the threaded spindle for expansion of the expansion means.

Preferably, the actuator is constructed such that it can be arranged and operated in the body tissue during the bone expansion. In this case, for example, the actuator can be operated from the outside, so that the patient's body can be closed completely after implantation of the expansion device and the actuator. For operation of the actuator, this has, for example, a switch which can be operated by exertion of pressure on the tissue lying on top or by application of a magnetic, electrical or electromagnetic field.

As a result of no elements having to be led out of the patient's body when implantation is complete, the risk of infection or of irritation of soft tissue is reduced.

If the medical apparatus comprises the expansion device in the embodiment with fillable chambers, a reservoir is preferably additionally provided for the medium which is pumped by the pump into the expansion device. Preferably, the reservoir is configured such that it is co-implanted into the body together with the expansion device and the actuator.

In this case, the reservoir can be a reservoir which can be filled with a needle. By this means the reservoir can be implanted in the empty state and then filled and/or refilled accordingly.

For example, the reservoir is a chamber, balloon or the like which is connected to a vascular access port system. The reservoir can be filled with the medium by puncturing the vascular access port system. For filling the reservoir, the vascular access port system is preferably punctured with a needle (Huber cut) and filled with the medium. Advantageously, by this means the vascular access port system closes again automatically after withdrawal of the needle and the medium thus remains within the reservoir. As can be seen from this, a particularly preferred medical apparatus which can be implanted completely into the body for bone expansion/callus distraction can be provided.

If the pump is not configured such that it can be implanted completely in the patient's body, the pump is, for example, an HPLC pump which is to be arranged outside the patient's body and allows delivery rates of the medium in the microliter range. The use of an HPLC pump is also advantageous because it renders possible constant delivery rates of the medium independently of the increase in pressure within the chambers.

The medical apparatus preferably also has a controller which can control the actuator such that the expansion means expand in a particular manner.

Preferably, the controller can control the actuator such that the expansion means expand in accordance with the principle of callus distraction.

The extension of a tubular bone can be controlled with the medical apparatus according to the invention. When the expansion device is inserted into a tubular bone slit in the longitudinal direction, the actuator can expand the expansion means of the expansion device such that the callus formed on the slit tubular bone is distracted and a tubular bone of larger diameter is obtained. For example, the actuator can be controlled via the controller such that the expansion device expands uniformly or non-uniformly Generally, the controller can also be configured as a feedback controller, wherein parameters measured on the expansion device, such as pressure, force, volume or lengths, can be used as input parameters in the controller for the feedback control.

Preferably, the medical apparatus comprises the expansion device in the embodiment of the expansion means as fillable chambers, the actuator in this case being a pump which is set up to fill the chambers with a medium, such as, for example, a liquid, a gel or a gas. The controller can control the pump for the bone expansion such that it fills the chambers of the expansion device with the medium for the expansion.

If the tubular bone to be expanded is of more stable or thicker construction at a particular position, the pump increases the pressure in the corresponding chamber of the expansion device such that this chamber expands together with the other chambers in a particular manner. The expansion of the chambers can be controlled, for example, by measuring/determining the volume of a liquid/gel passed into the chambers. If the medium passed into the chambers is compressible, for example if air is used, the pressure prevailing in the corresponding chamber is additionally also to be taken into consideration in the determination of the volume.

Preferably, the pump is controlled by the controller such that the expansion device expands in accordance with the principle of callus distraction. For example, the pump is controlled such that the callus would be expanded or distracted by 0.5 to 0.75 mm daily.

The formation or distraction of the callus can be monitored by sonography and the control of the expansion device can be adapted accordingly.

Preferably, a liquid which provides X-ray contrast or an inert liquid is used as the medium which is passed into the chambers by the pump. In the first case, after insertion of the expansion device into the tubular bone the position and the state of the expansion device can be readily determined, and in the second case the risk of the patient's health being endangered if the expansion device should have a leaking point can be reduced.

If the expansion device according to the invention and the actuator are configured such that they can be implanted completely into the patient's body, the controller is preferably set up such that it can control the actuator by application of a pressing force on the tissue lying over the actuator or by application of a magnetic/electrical/electromagnetic field.

For example, for this a cuff or the like which is connected to the controller and through which the controller can send and transmit control signals to the actuator is positioned at the corresponding position on the patient's body.

To accelerate the callus formation and maturing of the callus, an application of ultrasound can preferably be employed. Preferably, low-energy ultrasound is used, wherein it is possible to preferably introduce the ultrasound into the expansion device via the medium (liquid, gel or gas). For this, for example, an ultrasound generator can be arranged within the expansion device and/or within the pump for the introduction of the ultrasound into the medium. For example, the ultrasound is applied in pulsed form with a frequency of 1.5 MHz and an output of 30 mW/cm$^2$ (pulse frequency 1 kHz, signal length 200 µs).

In a preferred embodiment of the medical apparatus according to the invention, the controller is set up such that it can expand the expansion means continuously or stepwise.

Most preferably, the expansion device according to the invention and the medical apparatus are employed as intended for treating defects on thigh bones or shin bones, wherein, for reconstruction of the corresponding bone, the calf bone (fibula) is expanded by means of the expansion device according to the invention and then subjected to microvascular transfer for correction of the defect.

At the start of treatment an intramedullary access on the fibula head and an opening of the medullary space are created, the fibula then being slit in a length of, for example, 20 cm (longitudinal osteotomy). The expansion device according to the invention is then inserted into the fibula through the access. The expansion of the expansion device as a rule starts on the 7th day after the osteotomy, the callus distraction being performed by 0.5 to 0.75 mm daily.

Generally, as already explained above, the controller controls the expansion device such that this expands in accordance with the principle of callus distraction. The "principle of callus distraction" differs in many cases according to the patient's age and constitution. For example, the callus forms faster in children than in elderly patients, and for this reason the controller can be adjusted or programmed such that the "principle of callus distraction" can be readily adapted to the particular patient. For example, the controller is programmed such that preprogrammed and pre-prepared expansion methods are stored for various cases.

After a desired distraction of the callus, consolidation of the callus may take place over a further period of time of approximately 30 to 40 days. Overall, transfer of the made-up tubular bone by the microvascular technique can be carried out after a period of approximately 60 days after the start of the distraction.

The total duration of the callus distraction and the duration of treatment of tubular bone defects can be reduced considerably by the expansion device or medical apparatus according to the invention.

Preferred embodiments of the expansion device and of the medical apparatus are explained in the following with the aid of the attached figures.

FIG. 1A shows a diagram of a first preferred embodiment of a medical apparatus according to the invention, wherein the medical apparatus comprises a pump and an expansion device according to the invention connected to the pump.

FIG. 1C shows a medical apparatus according to a second preferred embodiment of the invention, wherein the medical apparatus differs from those shown in FIGS. 1A and 1B in that it comprises a differently configured expansion device.

FIG. 1D shows a variant of the medical apparatus according to the invention according to the second preferred embodiment of the invention.

FIG. 2C shows a diagram in cross-section of the expansion device shown in FIGS. 1C and 1D, wherein the cross-section shown corresponds to a first chamber of the expansion device.

FIGS. 3A and 3B show a diagram of a third preferred embodiment of a medical apparatus according to the invention, wherein in FIG. 3A an expansion device according to the invention of the medical apparatus is in a contracted or shrunk state and in FIG. 3B is in an expanded state.

FIGS. 6A and 6B show a fourth preferred embodiment of a medical apparatus according to the invention, wherein this embodiment differs from that shown in FIGS. 3A and 3B in that the expansion means are configured differently.

FIRST EMBODIMENT

Figure 1B:
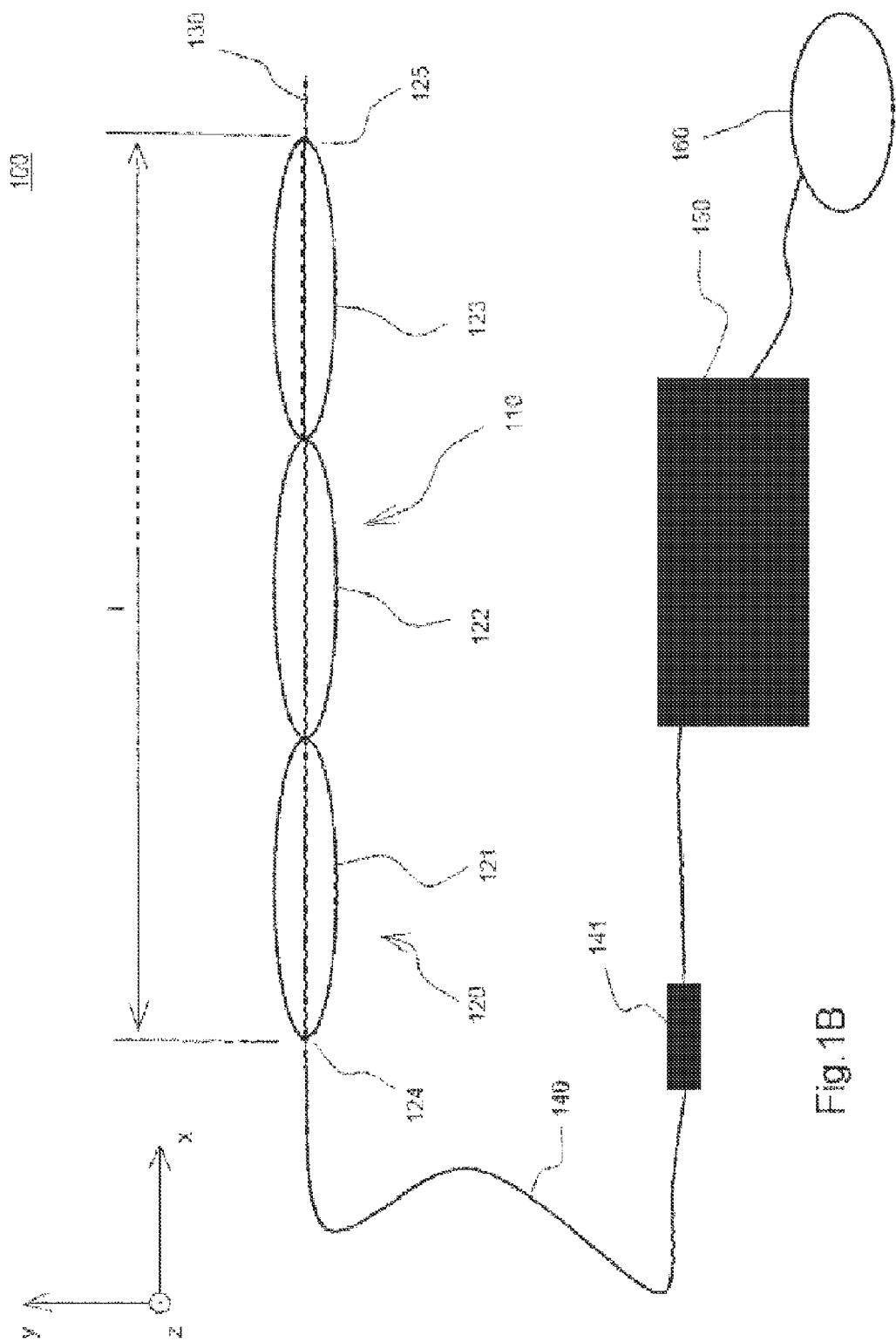
FIG. 1B shows a variant of the medical apparatus according to the invention according to the first preferred embodiment of the invention, wherein the medical apparatus differs from that shown in FIG. 1A in that the expansion device comprises no encasing element.

FIGS. 1A and 1B show a diagram of a first preferred embodiment of a medical apparatus 100 according to the invention for bone expansion.

The medical apparatus 100 comprises, in addition to the expansion device 110 according to the invention, a line 140 and an actuator 150 in the form of a pump, wherein the expansion device 110 is connected to the pump 150 via the line 140.

The expansion device 110 shown in FIG. 1A has an encasing element 120 formed as an encasing balloon, in which a plurality of expansion means 121, 122, 123 in the form of chambers are provided.

The encasing element 120 is produced from a flexible material, for example from a polyolefin-based elastomer, a silicone which is suitable for medical uses or generally from a resilient polymer. The encasing element 120 can expand together with the chambers 121, 122, 123 during the expansion described in the following.

The X direction shown in FIG. 1 corresponds to the longitudinal direction of the expansion device 110 according to the invention. The expansion device 110 extends in this longitudinal direction between a proximal 124 and a distal end 125.

The encasing element 120 likewise extends along this X direction shown in FIG. 1A and completely encloses the chambers 121, 122, 123.

Within the encasing element 120 runs a metal core 130, which preferably has a diameter of 1 mm. The metal core 130 is provided to increase the stability of the expansion device 110 and facilitates the insertion of the expansion device 110 into a tubular bone. Preferably, the metal core 130 is also constructed such that it has a good X-ray contrast. By this means the position of the expansion device 110 within the tubular bone can be readily checked.

The total length of the expansion device 110 shown in FIG. 1A is preferably between 8 and 25 cm. Its maximum diameter d in the contracted or shrunk state is 0.3 cm.

Within the encasing element 120, as already mentioned above, three chambers 121, 122, 123 are provided, which each independently and individually can be filled with a particular medium, such as, for example, a liquid, a gel or a gas.

In this first embodiment, the chambers 121, 122 and 123 are formed by identical balloons, which are arranged uniformly and directly in succession in the longitudinal direction shown in FIG. 1A.

When the chambers/balloons 121, 122 and 123 are filled with the medium, the balloons 121, 122, 123 expand radially in the Y-Z plane shown in FIG. 1A, as a result of which a force can in each case be exerted on a tubular bone via each chamber 121, 122, 123.

The encasing element 120 encloses the chambers 121, 122, 123 or balloons completely and in a sealed manner. As a result, the chambers 121, 122, 123 come into direct contact with no body elements, such as bones, bone marrow or body fluids. This has the advantage that the chambers 121, 122, 123 can have dimensions and be constructed from materials merely with respect to the maximum pressures or forces to be expected.

In this first preferred embodiment, the chambers/balloons 121, 122, 123 are constructed, for example, such that they can withstand a pressure of 25 bar.

At the proximal end 124 of the expansion device 110 three pressure tubes 142, 143, 144 (FIG. 2A), which are led in the line 140, enter into the expansion device 110. Each of the pressure tubes 142, 143, 144 opens in each case into one of the three chambers/balloons 121, 122, 123.

Via the particular pressure tubes 142, 143, 144, the medium can be guided into the corresponding chamber, as a result of which the expansion device 110 can be expanded radially (Y-Z plane) in sections in the longitudinal direction (X direction) shown in FIG. 1A. As can be seen from this, the chambers/balloons 121, 122, 123 can be filled with the medium independently of each other, and for this reason the expansion device 110 can be expanded in a particular manner.

In this first preferred embodiment, the chambers/balloons 121, 122, 123 are in each case connected indirectly or directly (fixed) to the metal core 130, so that the chambers/balloons 121, 122, 123 mainly expand in the radial direction (Y-Z plane) when the medium is introduced.

The line 140 leads from the proximal end 124 of the expansion device 110 to a connector element 141 (connection/disconnection element) which, when the medical apparatus 100 is used as intended, is arranged within the body tissue.

From the connector element 141 the line 140 runs further to the pump 150, which, when the medical apparatus is used as intended, is outside the patient's body.

This part of the line 140, i.e. from the connector element 141 to the pump 150, is preferably coated with an antibiotic coating and/or a silver coating to avoid bacterial colonization of the line 140.

The medium which is pumped by the pump 150 into the chambers/balloons 121, 122, 123 is contained in a reservoir 160. The reservoir 160 can be a part of the pump 150 or, as shown in FIG. 1A, a separate reservoir.

Alternatively, the medical apparatus 100 shown in FIG. 1A can preferably be configured such that the pump 150 and the reservoir 160 can be implanted into the patient's body together with the expansion device 110. In this case the expansion device 110, the line 140, the pump 150 and the reservoir 160 can be accommodated completely in the patient's body, and for this reason no lines or elements have to be led out of the patient's body and the patient's body can be closed completely after the implantation. This has the advantage that infections can be better prevented, since bacteria and/or viruses cannot enter into the patient's body through an entry point of the line.

For implantation into the body, the reservoir 160 is preferably formed from a flexible, resilient material and can expand to accommodate various amounts of the medium.

The volume of the reservoir 160 can vary according to what amount of the medium is to be accommodated therein. It is not absolutely necessary for the reservoir 160 to be implanted already in the filled state.

For filling the reservoir 160, a vascular access port system (not shown) can be provided thereon, which can be arranged in the patient's tissue such that it can be punctured with a needle and the medium can be passed into the reservoir 160. This embodiment of the reservoir 160 is also advantageous in that it can be readily refilled.

Figure 2A:
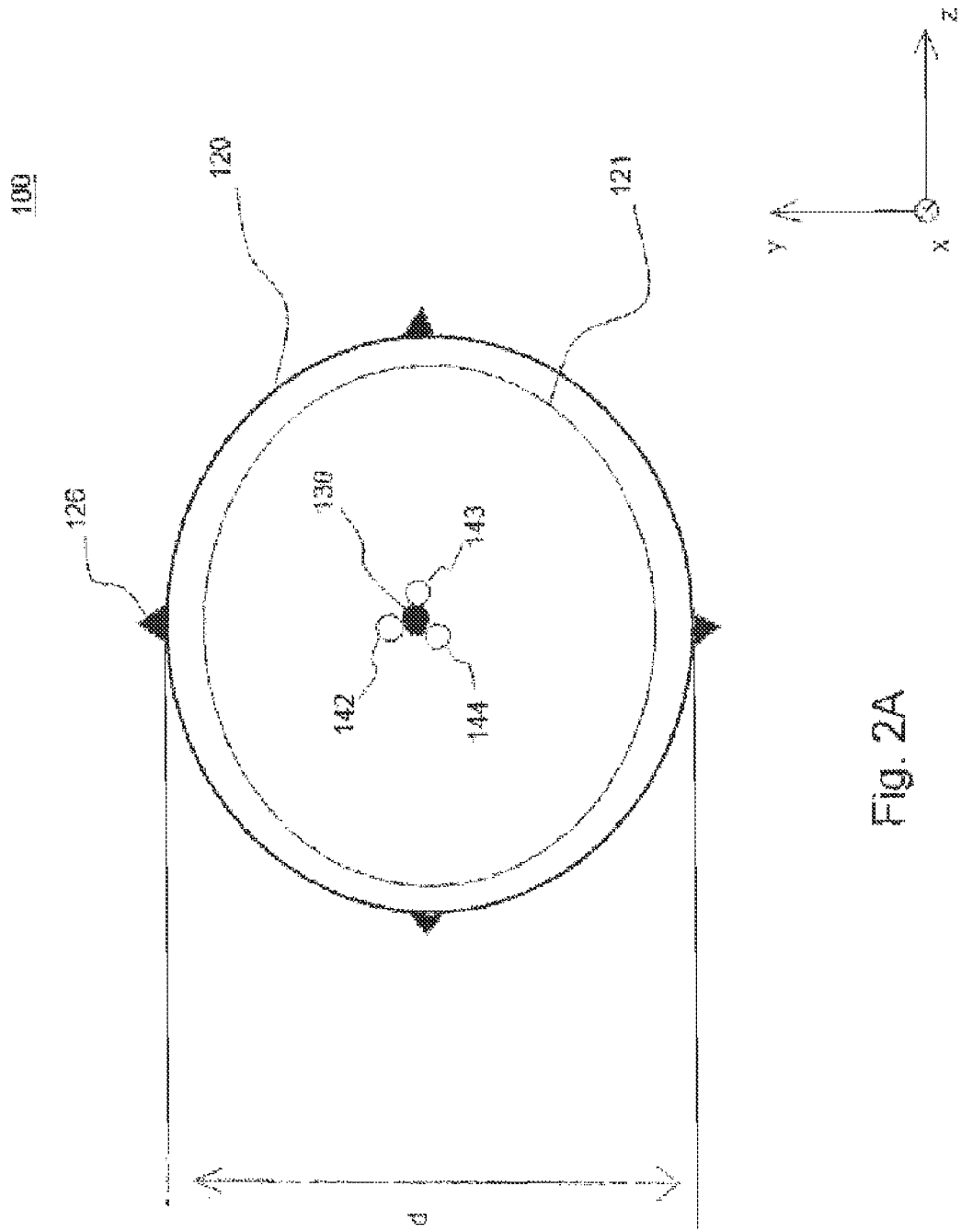
FIG. 2A shows a diagram in cross-section of the expansion device shown in FIG. 1A, wherein the cross-section shown corresponds to a first chamber of the expansion device.

FIG. 2A shows a diagram in cross-section of the expansion device 110 shown in FIG. 1A.

The chamber which can be seen in FIG. 2A corresponds to the chamber 121 shown in FIG. 1A, into which one of the pressure tubes 142, 143 144 for introduction of the medium opens and through which the remaining pressure tubes run to the corresponding chambers.

On the encasing element 120 preferably at least one protrusion 126—in this preferred embodiment four protrusions—is formed, which is provided so that the expansion device 110 retains its position in the inserted state. When the expansion device 110 according to the invention has been inserted into the medullary space via an intramedullary access and the expansion device 110 is expanded, the protrusions 126 ensure secure positioning of the expansion device 110 within the medullary space.

In a preferred construction, not shown, of the protrusion(s) 126, the pressure tubes 142, 143, 144 can be accommodated therein and run in the protrusion(s) to the corresponding chambers/balloons 121, 122, 123. This construction of the protrusion(s) 126 or this installation of the pressure tubes 142, 143, 144 has the advantage, for example, that the chambers 121, 122, 123 can be better fixed to the metal core 130, since none of the pressure tubes 142, 143, 144 has to be passed through at the connection between the chamber/balloon 121, 122, 123 and metal core 130.

The pump 150 shown in FIG. 1A is provided for pumping the particular medium from the reservoir 160 in each case into the chambers 121, 122, 123. Preferably, a liquid, such as, for example, a sodium chloride solution, water or a gel, is used as the medium to be introduced.

The pump 150 is preferably controlled by a controller (not shown). The controller can be co-accommodated in the pump 150 or also be a unit separate from the pump 150.

The controller can control the pump 150 such that this pumps the medium stepwise into the chambers and therefore the expansion device expands stepwise. By this means the pump can guide the medium in uniform steps, i.e. always the same amount of liquid, or in non-uniform steps, i.e. different amounts of liquid, into the chambers/balloons 121, 122, 123.

For example, the controller can be programmed such that it automatically pumps a defined amount of the medium from the reservoir 160 into the expansion device 110 at certain time intervals.

Alternatively, the controller can also control the pump 150 such that the pump expands the expansion device 100 or the chambers/balloons 121, 122, 123 continuously from a starting state.

Furthermore alternatively, the controller determines, for example, with the aid of the amount of liquid already guided into the chambers 121, 122, 123, the current volume of the expansion device 110 or of the chambers/balloons 121, 122, 123 and the amount of liquid necessary for a desired expansion of the expansion device 110 which is to be introduced into the chambers/balloons 121, 122, 123. The controller subsequently controls the pump 150 such that it pumps the amount of liquid to be introduced into the chambers/balloons 121, 122, 123.

Generally, the controller is preferably programmed such that it feeds the expansion device 110 with an amount of liquid such that this expands stepwise or continuously in accordance with the principle of callus distraction.

If the pump 150, the reservoir 160 and the expansion device are to be implanted together into the patient's body, the controller is preferably configured such that either it is co-accommodated in the pump 150 or it can control the pump 150 in a wireless manner.

For example, for wireless control the controller comprises a cuff which is arranged on a particular body part of the patient and via which the controller can transmit control signals to the implanted pump 150, for example by application of a magnetic, electrical or electromagnetic field.

The controller can also be configured as a feedback controller, wherein a parameter recorded by measurement, such as the pressure prevailing in the chambers or the volume thereof, is fed back to the controller for the feedback control.

As a result of the expansion device 110 having a plurality of chambers/balloons 121, 122, 123, different forces can be exerted on the tubular bones and the expansion device/tubular bone can be expanded in a particular manner.

FIG. 1B shows a variant of the medical apparatus 100 according to the invention according to the first preferred embodiment of the invention, wherein this differs from that shown in FIG. 1A only in that the expansion device 110 comprises no encasing element 127. In this variant of the expansion device 110, the chambers/balloons 121, 122, 123 come into direct contact with the bone to be expanded, and for this reason in this variant the chambers or the balloons 121, 122, 123 are configured with respect to the material such that they are suitable for direct contact with the bone or bone marrow.

Figure 2B:
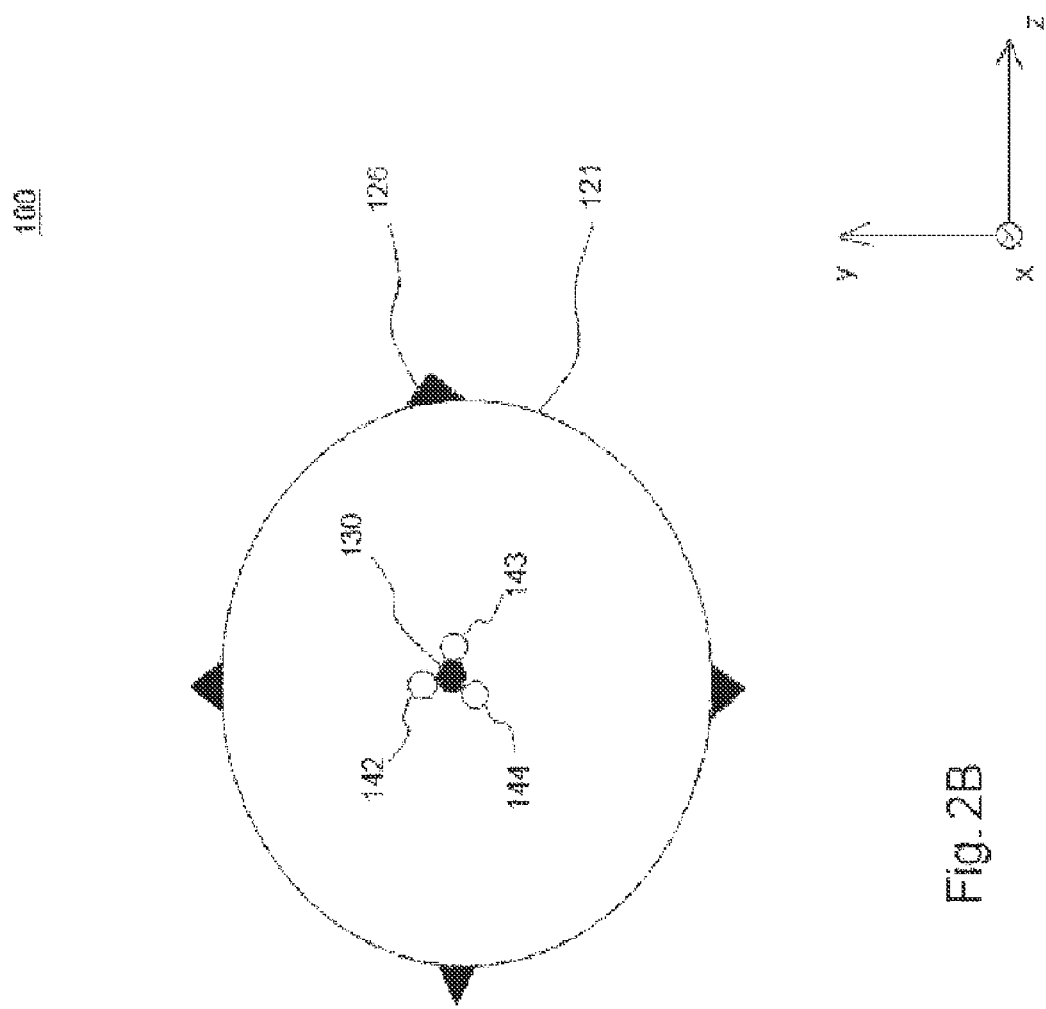
FIG. 2B shows a diagram in cross-section of the expansion device shown in FIG. 1B, wherein the cross-section shown corresponds to a first chamber of the expansion device.

FIG. 2B shows a diagram of a cross-section of the expansion device 100 according to the invention shown in FIG. 1B. The cross-section shown in FIG. 2B corresponds to a cross-section of the first chamber 121. Since this variant of the expansion device 110 according to the invention comprises no encasing element, the protrusions 126 are formed directly on the chambers/balloons 121, 122, 123 (in FIG. 2B on the chamber 121).

The remaining elements of the medical apparatus 100 shown in FIGS. 1B and 2B are identical to those described with reference to FIGS. 1A and 2A, and for this reason their description will not be repeated at this point.

Second Embodiment

FIG. 1C shows a second preferred embodiment of the medical apparatus according to the invention. The medical apparatus 200 shown in this figure differs from those described above in that the expansion device 210 is configured differently. In this second preferred embodiment, the expansion device 210 is formed by a tube 220, which is divided in the longitudinal direction (X direction) shown in FIG. 1C. For segmenting the tube, this can be filled, for example, with a silicone at appropriate points and closed such that the chambers 221, 222, 223 are formed.

FIG. 2C shows a cross-section of the expansion device 210 according to the invention shown in FIG. 1C. As can be seen from this, in this second embodiment the pressure tubes 142-144 likewise run through the chambers 221, 222, 223, each of the pressure tubes in each case opening into an assigned chamber 212, 222, 223.

Preferably, the tube 220 is constructed such that it does not have a constant internal diameter, and for this reason the wall thickness of the tube 220 changes. This is advantageous to the extent that during the expansion the tube 220 does not expand uniformly in all directions, and for this reason the expansion device 210 cannot be readily rotated within the bone marrow and remains fixed.

FIG. 1D shows a variant of the medical apparatus 200 according to the invention according to the second preferred embodiment of the invention, wherein this differs from that described with reference to FIG. 1C in that the tube 227 is divided into individual sections/tube pieces each assigned to a chamber. One of the chambers 221, 222, 223 is assigned to each tube piece.

In all the embodiments and variants of the medical apparatus shown with reference to FIG. 1A-1D, the pump 150, the line 140, the reservoir 160 and the controller are identical, and for this reason the explanations in this respect apply equally to all embodiments and variants of the medical apparatus according to the invention.

Third Embodiment

A third preferred embodiment of the medical apparatus for bone expansion is described in the following.

The medical apparatus 300 comprises an expansion device 310 for bone expansion.

FIGS. 3A and 3B show the expansion device 310 on the one hand in a shrunk or contracted state (FIG. 3A) and on the other hand in its expanded state (FIG. 3B).

The X direction shown in FIGS. 3A and 3B corresponds to the longitudinal direction of the expansion device 310 according to the invention, in which the expansion device 310 extends from a proximal end 324 to a distal end 325.

As shown in FIG. 3A, the expansion device 310 comprises three expansion means 321, 322, 323, which in this embodiment are formed as mechanical spring elements. The spring elements 321, 322, 323 are identical in construction.

The spring elements 321, 322, 323 each have a first leaf spring 3212, 3222, 3232 and a second leaf spring 3214, 3224, 3234, which each are fixed on the one hand to a first sleeve 3211, 3221, 3231 and on the other hand to a second sleeve 3213, 3223, 3233.

The spring elements 321, 322, 323 cooperate with a threaded spindle 330 such that the spring elements 321, 322, 323 or their leaf springs can be expanded. For this, the first and second sleeves are arranged on the threaded spindle 330 or the threaded spindle 330 is passed through the first and second sleeves.

The first sleeves 3211, 3221, 3231 and the threaded spindle 330 engage via a thread such that by rotation of the threaded spindle 330 the first sleeves 3211, 3221, 3231 can be displaced translatorially in the X direction on the threaded spindle 330. The state of the expansion device 310 in which the first sleeves 3211, 3221, 3231 are displaced is shown in FIG. 3B.

The second sleeves 3213, 3223, 3233 are mounted rotatably on the threaded spindle 330; however, they are not displaced by rotation of the threaded spindle 330 but remain fixed with respect to the longitudinal direction of the expansion device 310 (X direction) on rotation of the threaded spindle 330.

By this construction of the spring elements 321, 322, 323, on rotation of the threaded spindle 330 the first sleeves 3211, 3221, 3231 are displaced translatorially in the longitudinal direction shown in FIG. 3A (X direction), as a result of which they approach the second sleeves 3213, 3223, 3233 and the first and second leaf springs 3212, 3214, 3222, 3224, 3232, 3234 are bent outwards (positive and negative Y direction).

The expansion device 310 and the spring elements 321, 322, 323, respectively, consequently expand on rotation of the threaded spindle 330, a force being exerted via each spring element 321, 322, 323 on to the tubular bone for callus distraction when the expansion device 310 is arranged within a tubular bone to be expanded.

Depending on the dimensions of the spring elements 321, 322, 323, such as, for example, the choice of the spring constants and the lengths of the leaf springs, and the degree of displacement of the first sleeves 3211, 3221, 3231, a particular force can be exerted via each of the spring elements 321, 322, 323 on the tubular bone for callus distraction.

The threaded spindle 330 is preferably constructed such that it can be bent to a certain degree. By this means the arrangement of the expansion device 330 within a tubular bone through an intramedullary access is facilitated.

At the proximal end 324 of the expansion device 310 according to the invention a coupling means 326 shown in FIGS. 3A and 3B is provided, by which the expansion device 310 can be coupled with an actuator 350 via a flexible torsion transmission element 340.

In this third preferred embodiment, the actuator is realized by an electric motor which is operated by a controller (not shown) such that it rotates the threaded spindle 330 for extension of the expansion device 310.

As also in the first and second preferred embodiment, the actuator, i.e. the electric motor 350, can be configured such that this can be implanted into the patient's body together with the expansion device 310.

The controller can control the electric motor such that this rotates the threaded spindle 330 stepwise and therefore expands the spring elements 321, 322, 323 stepwise. By this means the electric motor 350 can rotate the threaded spindle 330 in uniform steps or in non-uniform steps.

For example, the controller can be programmed such that it automatically rotates the threaded spindle 330 by a defined amount at certain time intervals.

Alternatively, the controller can also control the electric motor 350 such that the expansion device 310 or the spring elements 321, 322, 323 are expanded continuously from a starting state.

As also in the above preferred embodiments, the controller controls/regulates the actuator or the electric motor such that it expands the expansion device 310 in accordance with the principle of callus distraction.

Preferably, for feedback control of the expansion of the expansion device 310, the force necessary for rotation of the threaded spindle 330, from which the forces exerted on the tubular bones by the spring elements 321, 322, 323 can be concluded, is determined and used for the feedback control (and returned to the controller, respectively).

Figure 4:
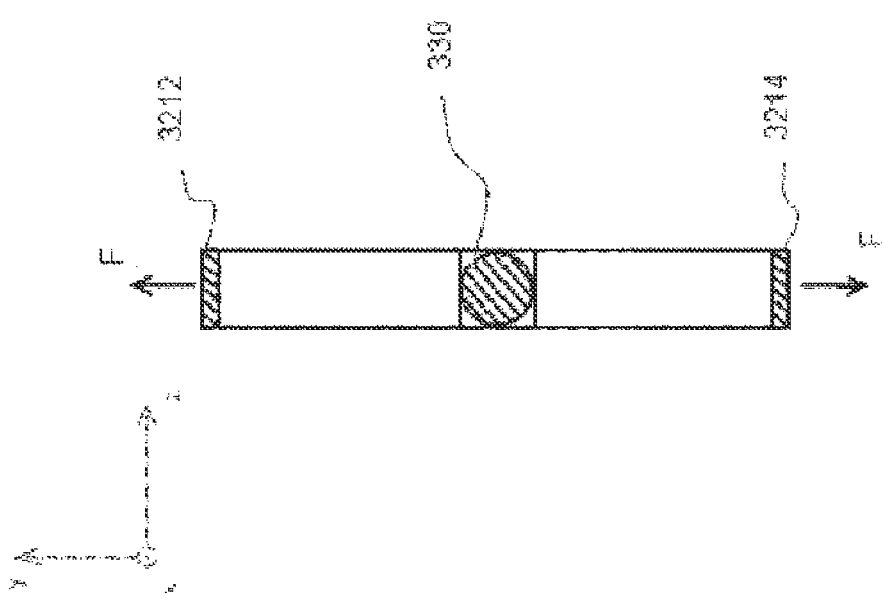
FIG. 4 shows a diagram in cross-section of the expansion device according to the invention according to the third preferred embodiment of the medical apparatus, wherein the expansion means shown comprises two leaf springs.

FIG. 4 shows a diagram of a section of the expansion device 310 according to the invention along the section line 4-4 shown in FIG. 3B.

As can be seen from this, the forces F can be exerted via the leaf springs 3212, 3214, which expand in the Y direction shown, on a tubular bone in which the expansion device 310 is arranged.

For production of the expansion means and the spring elements 321, 322, 323, respectively, hollow profiles (tubes or polygons) into which the threaded spindle 330 can be inserted are preferably used. The hollow profiles are (partially) slit on two opposite sections running in the longitudinal direction (X direction) such that the end sections of the hollow profiles lying in the longitudinal direction form the first and second sleeve. The sections lying between the sleeves and running in the longitudinal direction form the leaf springs.

To prevent overloading of the spring elements 321, 322, 323, stops can preferably be provided on the first and/or second sleeves, which stops come to rest when the first sleeves 3211, 3221, 3231 are displaced beyond a certain extent. The stops are preferably arranged between the leaf springs in the Y-Z plane shown in FIG. 4. To this extent the stops can also be cut out of the hollow profile during production of the spring elements.

Preferred modifications of the third preferred embodiment of the medical apparatus 300 and of the expansion device 310 are also explained in the following.

Figure 5:
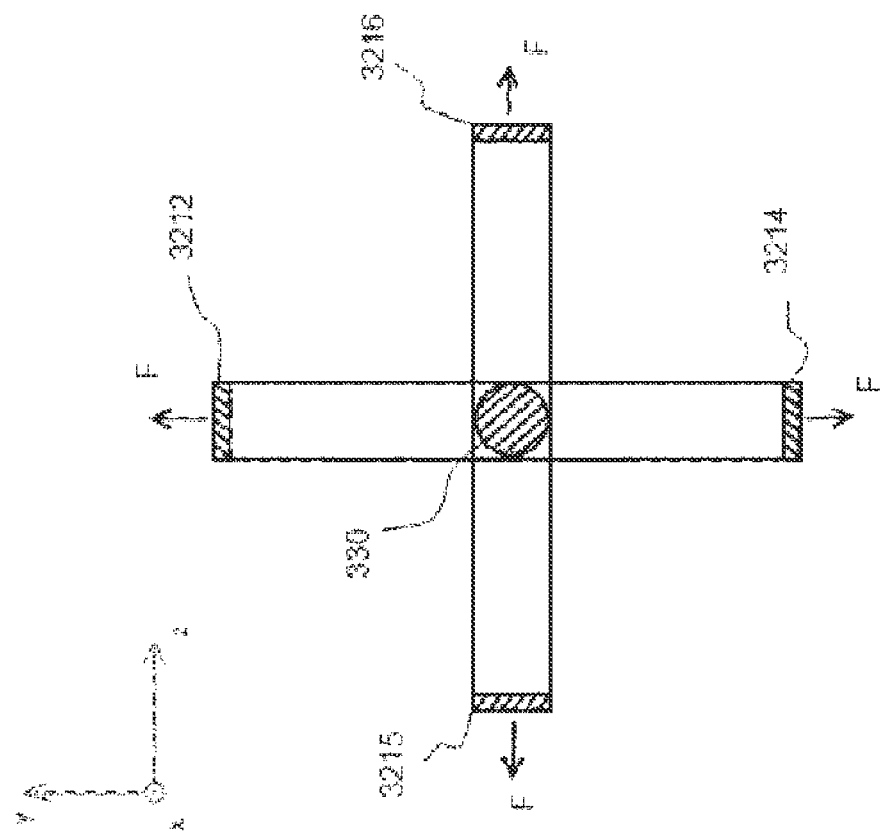
FIG. 5 shows a diagram in cross-section of the expansion device according to the invention according to the third preferred embodiment of the medical apparatus, wherein the expansion means shown comprises four leaf springs.

In general, as shown by way of example in FIG. 5 on the first spring element 321, the spring elements 321, 322, 323 can also have a plurality of leaf springs, for example three or four leaf springs.

As can be seen from FIG. 5, the third and fourth leaf springs 3215, 3216 are arranged displaced by 90° (around the axis of the threaded spindle 330) relative to the first and second leaf springs 3212, 3214. The third and fourth leaf springs 3215, 3216 are likewise fixed on the first and second sleeve 3211, 3213. When the threaded spindle 330 is rotated, the third and fourth leaf springs 3215, 3216 are bent outwards similarly to the first and second leaf springs 3212, 3214, and the corresponding spring element 321 is expanded, respectively.

The spring elements 321, 322, 323 have been described above as identical. However, the invention is not limited to this. The spring elements 321, 322, 323 can also be different. For example, the spring constants of the leaf springs assigned to one spring element or different spring elements can be different.

Furthermore, the spring elements 321, 322, 323 can be configured such that the corresponding second sleeves 3213, 3223, 3233 also engage with the threaded spindle 330 via a thread. In this case it is necessary for the threaded spindle 330 to have in the portion assigned to one of the spring elements a thread running opposite such that, depending on the direction of rotation of the threaded spindle 330, the particular first and second sheaths either approach one another or are displaced in the opposite direction.

As can be seen from the above description of the third preferred embodiment, the spring elements 321, 322, 323 to be expanded have uniform or different dimensions depending on the nature of the tubular bone to be expanded, so that the tubular bone in which the expansion device 310 is arranged can be expanded in a particular manner—preferably in accordance with the principle of callus distraction.

Fourth Embodiment

FIGS. 6A and 6B show a fourth embodiment of the medical apparatus according to the invention.

The elements of the fourth preferred embodiment of the medical apparatus 400 which are identical to those of the third preferred embodiment have the same reference numerals and are not explained again.

The medical apparatus 400 differs from that explained with reference to FIGS. 3A and 3B in that the expansion means of the expansion device 410 are not spring elements but are constructed as scissor elements 421, 422, 423.

The expansion device 410 likewise comprises three expansion means 421, 422, 423, wherein instead of the leaf springs, the corresponding sheaths 3211, 3213, 3221, 3223, 3231, 3233 are connected to one another via struts. The expansion means, i.e. the scissor elements 421, 422, 423, are identical in construction, and for this reason these are described only with reference to the first scissor element 421.

The struts 4211, 4212, 4213, 4214 of the first scissor element 421 on the one hand are fixed in a rotatably mounted manner on the sleeves 3211, 3213 and on the other hand are connected to one another in a rotatably mounted manner at a common connection point 4215, 4216.

When the threaded spindle 330 is rotated, this leads to a displacement of the sheath 3211, as a result of which the rotatably mounted struts 4211, 4212, 4213, 4214 are deflected outwards (in FIGS. 6A and 6B in the Y direction).

The struts 4211, 4212, 4213, 4214 carry on their common connection points 4215, 4216 in each case a force distribution element 424, 425, via which the scissor element 421 can exert the force for bone expansion or for callus distraction on the bone on rotation of the threaded spindle 330, the force distribution elements 424, 425 being configured such that they distribute the exerted force over the surface.

In this embodiment the force distribution elements 424, 425 are constructed as force distribution struts which in each case run in the longitudinal direction (X direction) and are supported/held by the scissor elements 421, 422, 423 in succession in the longitudinal direction. The force distribution struts 424, 425 are here in each case fixed to the connection points of the struts of the first to third scissor element, so that the force distribution struts 424, 425 are raised uniformly on rotation of the threaded spindle 330 and extension of the scissor elements 421, 422, 423.

In FIGS. 6A and 6B the scissor elements 421, 422, 423 are constructed such that they expand in the Y direction like the leaf springs shown in FIG. 4.

Nevertheless, the scissor elements 421, 422, 423 can also have additional struts, which are displaced by 90° as also are the leaf springs shown in FIG. 5. By this means, the force exerted on the bone for bone expansion can be better distributed.

The additional struts can likewise carry a force distribution element or a force distribution strut on their connection points.

If the force distribution elements are constructed as the force distribution struts 424, 425 shown, the force distribution struts 424, 425 preferably have a cross-section in the form of an arc of a circle (Y-Z plane) such that the force distribution struts 424, 425 form a casing of closed cross-section in the completely contracted state of the expansion device 410.

As can be seen from the descriptions of the expansion devices according to the invention and the medical apparatuss according to the invention, devices for a faster bone expansion/callus distraction can be provided.

The invention claimed is:

1. A method comprising:
    inserting an expansion device into a crevice of a bone, wherein the expansion device has a plurality of expansion chambers arranged along a longitudinal direction of the expansion device;
    expanding the expansion chambers to exert a radial force on the bone;
    controlling the expanding in accordance with the principle of callus distraction such that the expanding occurs over a plurality of days.

2. The method according to claim 1, wherein the expanding comprises expanding the expansion chambers uniformly.

3. The method according to claim 1, wherein the expanding comprises expanding the expansion chambers non-uniformly.

4. The method according to claim 1, wherein the expanding comprises filling the expansion chambers with a liquid.

5. The method according to claim 1, wherein the expanding comprises expanding the expansion chambers continuously over the plurality of days.

6. The method according to claim 1, wherein the expanding comprises expanding the expansion chambers stepwise over the plurality of days.

* * * * *